US00PP35739P2

(12) United States Plant Patent
Bean et al.

(10) Patent No.: US PP35,739 P2
(45) Date of Patent: Apr. 9, 2024

(54) ***DIETES* PLANT NAMED 'DBV001'**

(50) Latin Name: *Dietes bicolor*
Varietal Denomination: DBV001

(71) Applicant: De Wet Plant Breeders, Johannesburg (ZA)

(72) Inventors: Quinton Bean, Northriding (ZA); Charles Andrew De Wet, Sandton (ZA)

(73) Assignee: DE WET PLANT BREEDERS, Johannesburg (ZA)

( * ) Notice: Subject to any disclaimer, the term of this patent is extended or adjusted under 35 U.S.C. 154(b) by 0 days.

(21) Appl. No.: 18/242,307

(22) Filed: Sep. 5, 2023

(51) Int. Cl.
*A01H 5/02* (2018.01)
*A01H 6/00* (2018.01)

(52) U.S. Cl.
USPC ..... Plt./310

(58) Field of Classification Search
USPC ..... Plt./310
CPC ..... A01H 5/02; A01H 5/00; A01H 6/00
See application file for complete search history.

*Primary Examiner* — June Hwu
(74) *Attorney, Agent, or Firm* — Penny J. Aguirre

(57) ABSTRACT

A new cultivar of *Dietes bicolor* plant named 'DBV001' that is characterized by its foliage that is distinctly variegated with shades of green and creamy white, its flowers that are soft yellow in color with bright orange and dark brown blotches, its good sun resistance, its robust growing habit, and its compact plant habit.

3 Drawing Sheets

Botanical classification: *Dietes bicolor.*
Cultivar designation: 'DBV001'.

BACKGROUND OF THE INVENTION

The present invention relates to a new and distinct cultivar of *Dietes bicolor* known as *Dietes bicolor* 'DBV001' and is hereinafter referred to by the cultivar name 'DBV001'. The new cultivar of African Iris grown for use as a landscape and container plant.

The new cultivar arose from on ongoing breeding program by the Inventors in Johannesburg, South Africa. The goal of the breeding program is to develop unique cultivars of *Dietes* with compact plant habits. 'DBV001' arose from crosses made in 2011 between unpatented and unnamed proprietary plants of *Dietes bicolor* from the Inventors' breeding program as both female and male parent. The seeds were pooled for the crosses and therefore the exact parents are unknown. 'DBV001' was selected as a single unique plant in 2014 from amongst the seedlings derived from the above crosses.

Asexual reproduction of the new cultivar was first accomplished by division by one of the Inventors in Johannesburg, South Africa in 2017. Asexual reproduction of the new cultivar by division and tissue culture using meristematic tissue has shown that the unique features are stable and reproduced true to type in successive generations.

SUMMARY OF THE INVENTION

The following traits have been repeatedly observed and represent the characteristics of the new cultivar. These attributes in combination distinguish 'DBV001' as a new and unique cultivar of *Dietes.*

1. 'DBV001' exhibits foliage that is distinctly variegated with shades of green and creamy white.
2. 'DBV001' exhibits flowers that are soft yellow in color with bright orange and dark brown blotches.

3. 'DBV001' exhibits good sun resistance.
4. 'DBV001' exhibits a robust growing habit.

'DBV001' can be most closely compared to *Dietes grandiflora* cultivars 'Variegata' (not patented), 'Sun Stripe' (not patented) and 'White Tiger' (not patented). 'Variegata' differs from 'DBV001' in having narrower foliage, less distinct and less stable variegation, a less compact plant habit and flowers that are white in color. 'Sun Stripe' differs from 'DBV001' in having white flowers with purple markings and foliage with stripes that are more chartreuse and creamy yellow. 'White Tiger' differs from 'DBV001' in having foliage with white and green stripes and in having white flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Southern Living Plants, Sunset Plant Collection, Plantago, and Plant Development Services.

BRIEF DESCRIPTION OF THE DRAWINGS

The accompanying color photographs illustrate the overall appearance and distinct characteristics of the new *Dietes*. The photographs were taken of a plant 18-months in age of the new cultivar as grown in 2-gallon containers outdoors in Loxley, Alabama.

The photograph in FIG. 1 provides a view of a plant of 'DBV001' in bloom.

Figure 1:
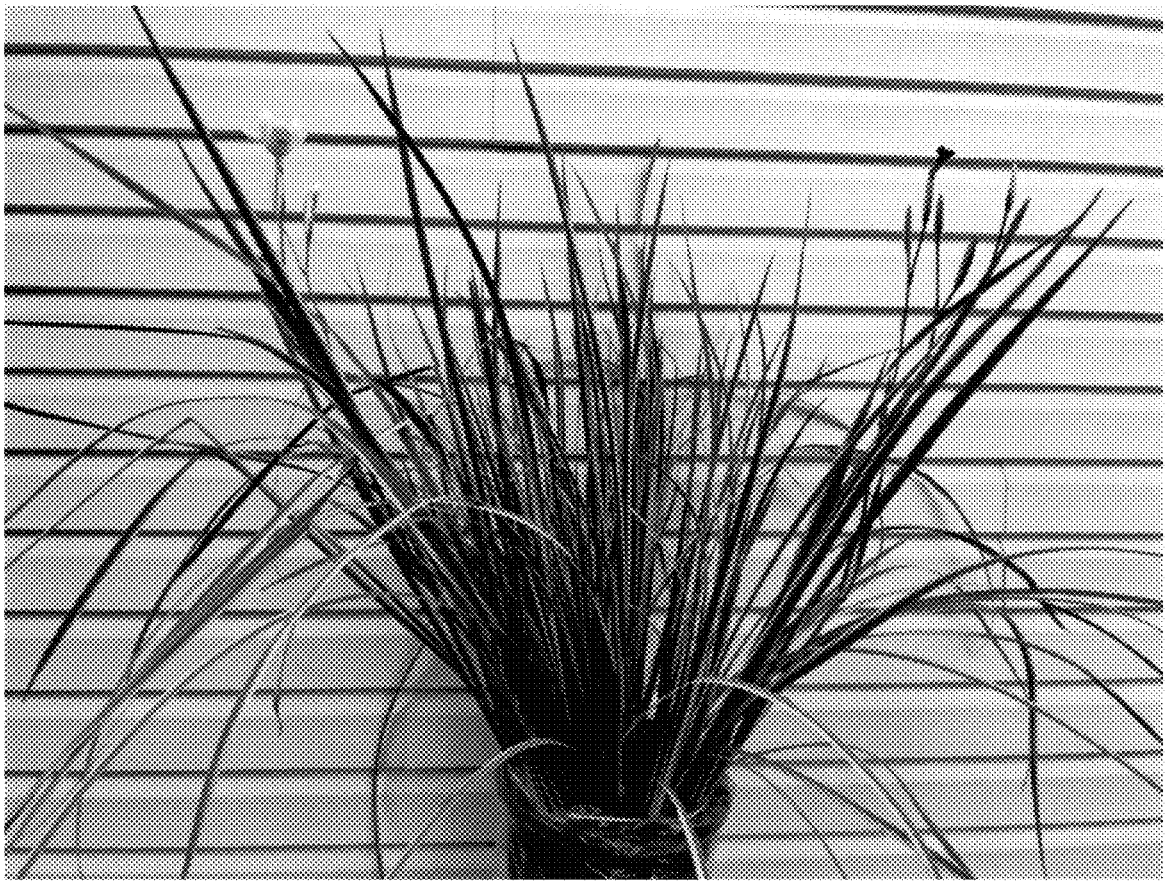
Figure 2:
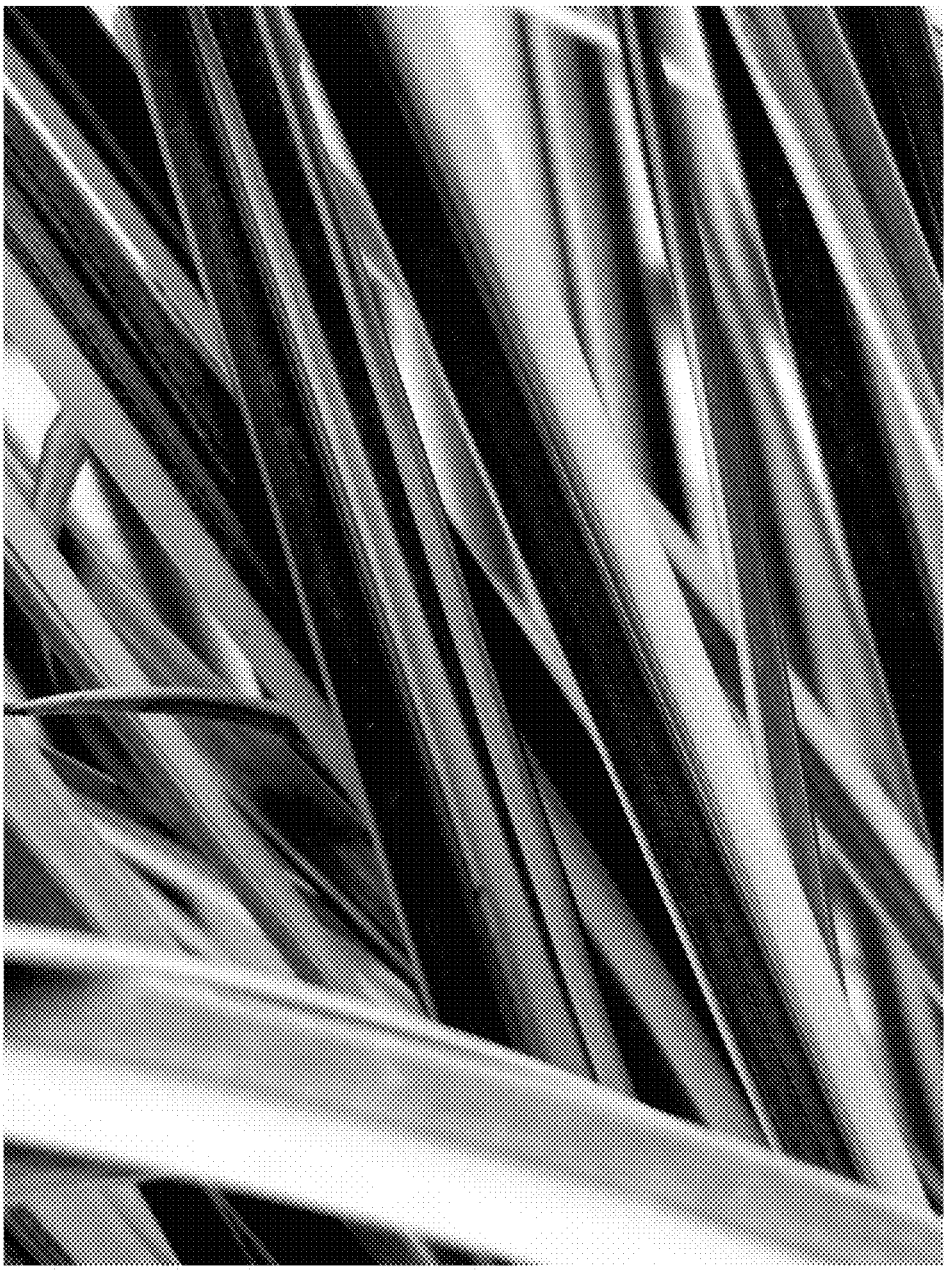

The photograph in FIG. 2 provides a close-up view of the foliage of 'DBV001'.

Figure 3:
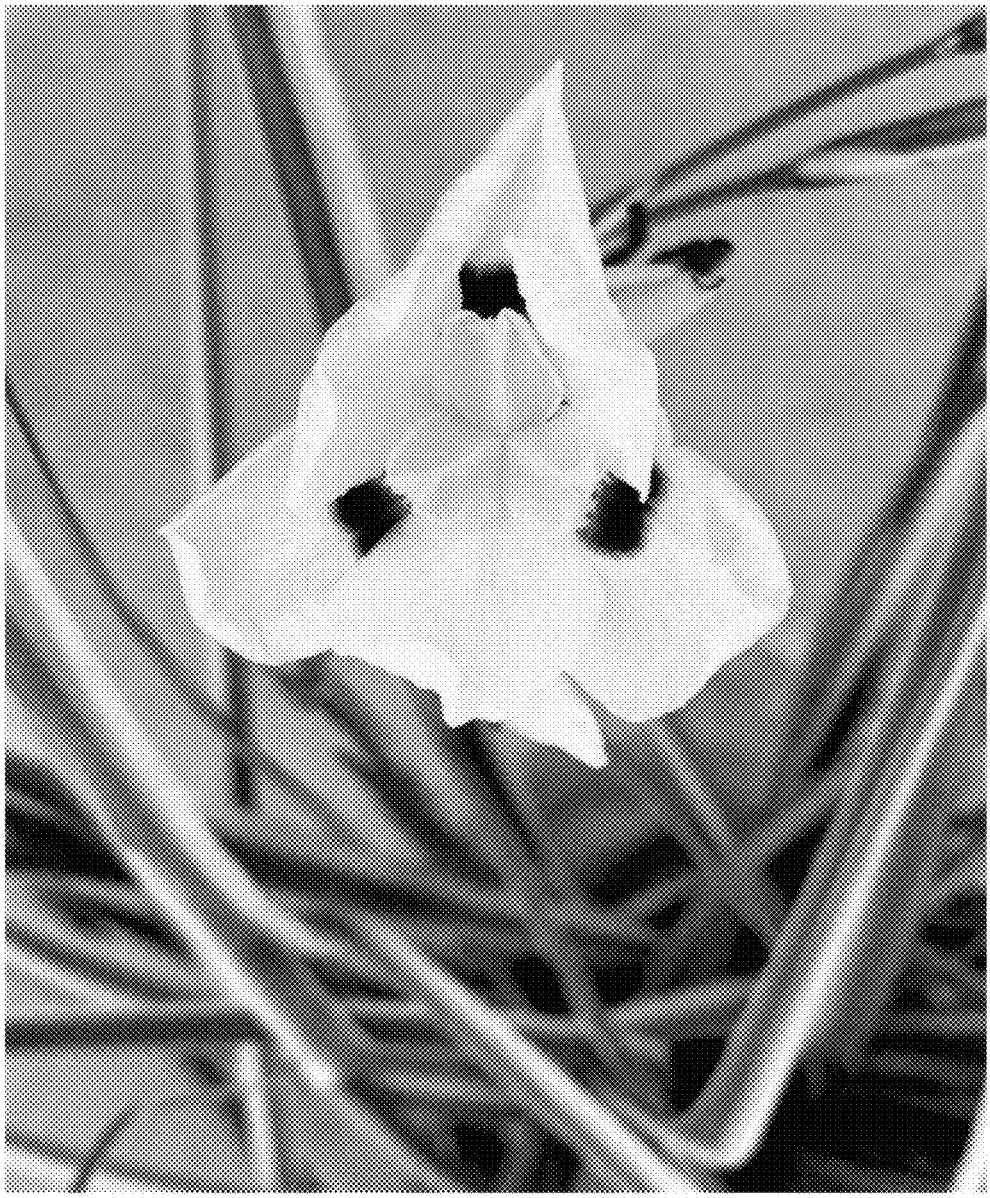

The photograph in FIG. 3 provides a close-up view of a flower of 'DBV001'.

The colors in the photographs may differ slightly from the color values cited in the detailed botanical description, which accurately describe the colors of the new *Dietes*.

DETAILED BOTANICAL DESCRIPTION OF THE PLANT

The following is a detailed description of plants 18-months in age cultivar as grown in 2-gallon containers outdoors in Loxley, Alabama. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—May to September in South Africa.

*Plant habit.*—Herbaceous perennial, clump-forming, upright, produces fan-shaped distichous shoots.

*Height and spread.*—About 76 cm in height and 87 cm in width as grown in a 2-gallon container.

*Hardiness.*—At least in U.S.D.A Zones 9 to 11.

*Culture.*—Observed to have good sun tolerance.

*Diseases and pests.*—No susceptibility to diseases or pests has been observed.

*Root description.*—Rhizomes with fine, fibrous roots.

*Propagation.*—Division and tissue culture.

*Root development.*—An average of 3 months to produce a rooted division and an average of 1 year to fully root in a P9 container.

*Growth rate.*—Vigorous, robust.

Foliage description:

*Leaf quantity.*—Average of 100 in a 2-gallon container.

*Leaf shape.*—Ensiform.

*Leaf division.*—Simple.

*Leaf base.*—Sheathed to base of stem in a zig-zag formation.

*Leaf apex.*—Very narrowly acute to a fine point.

*Leaf venation.*—Longitudinal, parallel, not prominent, fibrous, same color as leaves.

*Leaf margins.*—Entire.

*Leaf attachment.*—Sheathed.

*Leaf arrangement.*—Comprises a fan with new growth emerging from center of fan.

*Leaf orientation.*—Held upright and slightly pendulant once matured.

*Leaf surface.*—Smooth in texture, matte and longitudinally ridged.

*Leaf color.*—Young leaves both surfaces; variegated with a blend of 143C to 143D, 160C and 10B, mature leaves both surfaces; variegated with a blend of 147A, 147B, 147C, 160C and 10B.

*Leaf size.*—Mature to about 76 cm in length and 1.2 cm in width.

Flower scape description (peduncle):

*Scape shape.*—Round to slightly ovoid.

*Scape number.*—One per mature fan (branched).

*Scape aspect.*—Primary; straight, secondary; held upright to about 30° to 40° from vertical.

*Scape branching.*—3 secondary branches.

*Scape size.*—Primary; 45 cm in length, 3 mm in width, secondary; ranges from 7 cm in length with an average of 2 mm in width.

*Scape color.*—147A.

*Scape surface.*—Glabrous, very strong, matte.

*Scape bracts.*—On secondary peduncles, an average of 2.5 cm in length and 3 mm in diameter, color; 147A and 159D, shape, margins, and apex; similar to leaves.

Flower description:

*Inflorescence type.*—Single flowers on axillary and terminal peduncles, perianth comprised of six tepals, 3 larger outer tepals and 3 inner tepals, petaloid style arms with crested stigmatic lobes.

*Inflorescence size.*—17 cm in height, 9 cm in width.

*Lastingness of flowers.*—3 days.

*Flower fragrance.*—None.

*Flower number.*—6 per scape.

*Flower bud.*—Narrowly elliptical in shape, acute apex, rounded base, 3.5 cm in length, 1.5 mm in width, 4B in color, surface is glabrous and velvety.

*Flower aspect.*—Upright to outward.

*Spathes.*—3.5 cm in width and 6 mm in length, flower buds are completely encircled by a tough, leathery sheathing bract that is glabrous and matte, color; 160B, sometimes with vertical stripes of NN137A.

*Flower size.*—4 cm in diameter, 2 cm in depth.

*Tepal shape.*—Outer tepals broadly ovate, inner tepals spatulate.

*Tepal base* (*outer and inner*).—Truncate.

*Tepal apex* (*outer and inner*).—Nearly round with bifid, bluntly pointed at tips.

*Tepal surface* (*outer and inner*).—Glabrous and smooth, slightly velvety.

*Tepal margin* (*outer and inner*).—Entire, undulate.

*Tepal aspect.*—Outer tepal reflexed from mid-section, inner tepals nearly horizontal.

*Tepal size.*—Outer tepals; 2.5 cm in length and 2 cm in width cm in width, inner tepals; about 1.5 cm in length and 8 mm in width.

*Tepal color.*—Outer tepal; when opening and fully open inner surface; 8B, mottled with rounded to oval shaped spots from base to midsection; N30D, midsection has a heart shaped blotch 200A surrounded by N30D, when opening and fully open lower surface; 11D, inner tepal; when opening and fully open upper and lower surface; 11D.

Reproductive organs:

*Gynoecium.*—1 pistil, style; 3-branched, showy, petaloid, branches are 7 mm in length and 1.2 cm in width, entire margins with bifurcate apex, both surfaces slightly translucent and 11C in color, stigma; downward crescents, 11C in color, ovary; inferior, 1 cm in length and 5 mm in width and 1A in color.

*Androecium.*—Stamens; 3, tucked under style arms, filaments; flattened and slightly curved, slightly translucent and glossy, 5 mm in length, 2 mm in width, NN155C in color, anthers; linear in shape, basifixed, 3 mm in length, 1.5 mm in width, 158A to 161A in color, pollen; moderate, NN155B in color.

*Seed.*—Capsule development has not been observed to date.

It is claimed:

1. A new and distinct cultivar of *Dietes* plant named 'DBV001' as herein illustrated and described.

* * * * *